(12) United States Patent
Sniffin et al.

(10) Patent No.: US 10,258,318 B2
(45) Date of Patent: *Apr. 16, 2019

(54) SYSTEM AND METHOD FOR PERFORMING SURGICAL PROCEDURES WITH A MODULAR SURGICAL SYSTEM HAVING A RAIL MECHANISM

(71) Applicant: Covidien LP, Mansfield, MA (US)

(72) Inventors: Kevin Sniffin, Roxbury, CT (US); Eric Taylor, Southington, CT (US); Emily Davis, Cheshire, CT (US); Peter Hathaway, Lebanon, CT (US)

(73) Assignee: Covidien LP, Mansfield, MA (US)

( * ) Notice: Subject to any disclaimer, the term of this patent is extended or adjusted under 35 U.S.C. 154(b) by 0 days.

This patent is subject to a terminal disclaimer.

(21) Appl. No.: 15/645,859

(22) Filed: Jul. 10, 2017

(65) Prior Publication Data
US 2017/0303904 A1 Oct. 26, 2017

Related U.S. Application Data

(63) Continuation of application No. 13/412,055, filed on Mar. 5, 2012, now Pat. No. 9,700,288.
(Continued)

(51) Int. Cl.
*A61B 17/00* (2006.01)
*A61B 90/50* (2016.01)
(Continued)

(52) U.S. Cl.
CPC ........ *A61B 17/00234* (2013.01); *A61B 90/50* (2016.02); *A61B 90/92* (2016.02); *A61B 90/94* (2016.02); *A61B 2017/00022* (2013.01); *A61B 2017/0046* (2013.01); *A61B 2017/00318* (2013.01); *A61B 2017/00398* (2013.01); *A61B 2017/00464* (2013.01); *A61B 2017/00734* (2013.01); *A61B 2017/2906* (2013.01); *A61B 2017/2908* (2013.01);
(Continued)

(58) Field of Classification Search
CPC .............. A61B 17/00234; A61B 19/26; A61B 2017/0046
See application file for complete search history.

(56) References Cited

U.S. PATENT DOCUMENTS 5,658,249 A 8/1997 Beland et al.
5,752,972 A 5/1998 Hoogeboom
(Continued)

*Primary Examiner* — Joseph M Dietrich

(57) ABSTRACT

A surgical system is provided including a reusable handle assembly having a controller and a reusable cannula assembly configured to be operatively connected to and steerable by the reusable handle assembly. The surgical system also includes a rail mechanism configured to cooperate with a port inserted through an incision, the rail mechanism mechanically attached to a stable platform. A plurality of surgical instruments are configured to be inserted through the reusable handle assembly and configured to advance a length of the reusable cannula assembly, such that the plurality of surgical instruments are engaged with at least one trigger mechanism of the reusable handle assembly. The handle assembly, the cannula assembly, and the plurality of surgical instruments are modular components configured to be releasably coupled to each other. The reusable cannula assembly slidably engages the rail mechanism to extend through the port and into the incision.

20 Claims, 3 Drawing Sheets

Related U.S. Application Data

(60) Provisional application No. 61/468,858, filed on Mar. 29, 2011.

(51) Int. Cl.
    *A61B 90/92*      (2016.01)
    *A61B 90/94*      (2016.01)
    *A61B 17/29*      (2006.01)
    *A61B 17/34*      (2006.01)
    *A61B 34/00*      (2016.01)
    *A61B 90/57*      (2016.01)
    *A61B 90/00*      (2016.01)

(52) U.S. Cl.
    CPC . *A61B 2017/3447* (2013.01); *A61B 2034/742* (2016.02); *A61B 2090/0808* (2016.02); *A61B 2090/0813* (2016.02); *A61B 2090/571* (2016.02)

(56) References Cited

U.S. PATENT DOCUMENTS

| | | |
|---|---|---|
| 5,827,319 A | 10/1998 | Carlson et al. |
| 5,931,849 A | 8/1999 | Desvignes et al. |
| 5,954,259 A | 9/1999 | Viola et al. |
| 6,090,107 A | 7/2000 | Borgmeier et al. |
| 6,248,092 B1 | 6/2001 | Miraki et al. |
| 7,044,937 B1 | 5/2006 | Kirwan et al. |
| 7,193,519 B2 | 3/2007 | Root et al. |
| 7,468,041 B2 | 12/2008 | Rhodes et al. |
| 7,727,255 B2 | 6/2010 | Taylor et al. |
| 7,757,925 B2 | 7/2010 | Viola et al. |
| 7,922,063 B2 | 4/2011 | Zemlok et al. |
| D649,635 S | 11/2011 | Cronin et al. |
| 9,700,288 B2 | 7/2017 | Sniffin et al. |
| 2001/0031983 A1 | 10/2001 | Brock et al. |
| 2002/0165549 A1 | 11/2002 | Owusu-Akyaw et al. |
| 2005/0096646 A1 | 5/2005 | Wellman et al. |
| 2006/0278681 A1 | 12/2006 | Viola et al. |
| 2007/0005002 A1 | 1/2007 | Millman et al. |
| 2008/0114342 A1 | 5/2008 | Whayne et al. |
| 2008/0262515 A1 | 10/2008 | Makower et al. |
| 2009/0048612 A1 | 2/2009 | Farritor et al. |
| 2010/0069936 A1 | 3/2010 | Palmer et al. |
| 2011/0130787 A1 | 6/2011 | Cinquin et al. |
| 2011/0251606 A1 | 10/2011 | Kerr |
| 2011/0251632 A1 | 10/2011 | Deville et al. |
| 2011/0257650 A1 | 10/2011 | Deville et al. |
| 2012/0095498 A1 | 4/2012 | Stefanchik et al. |

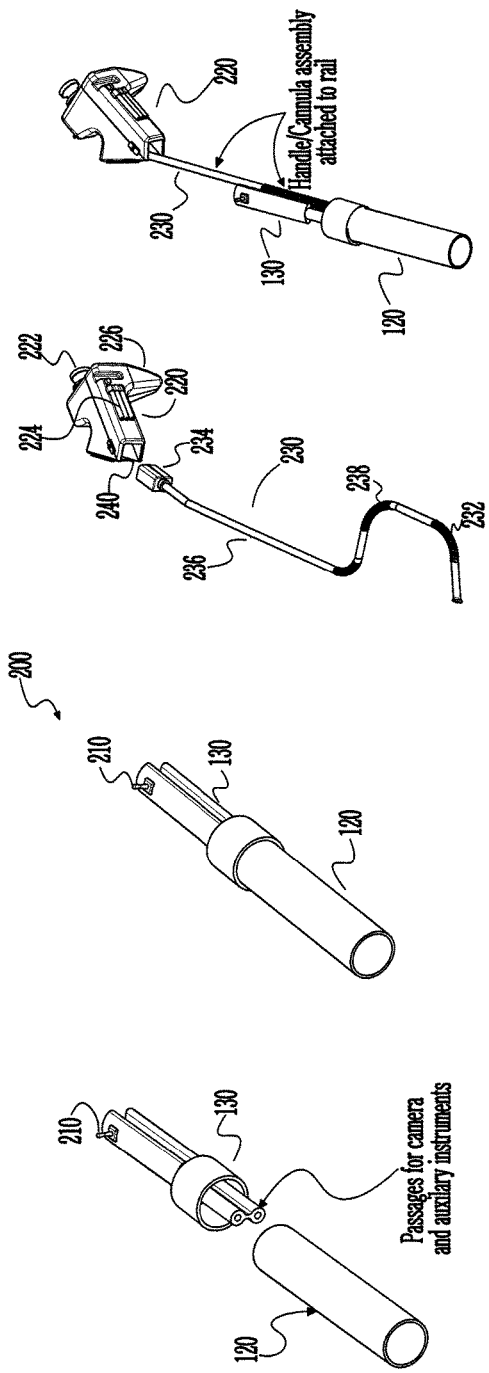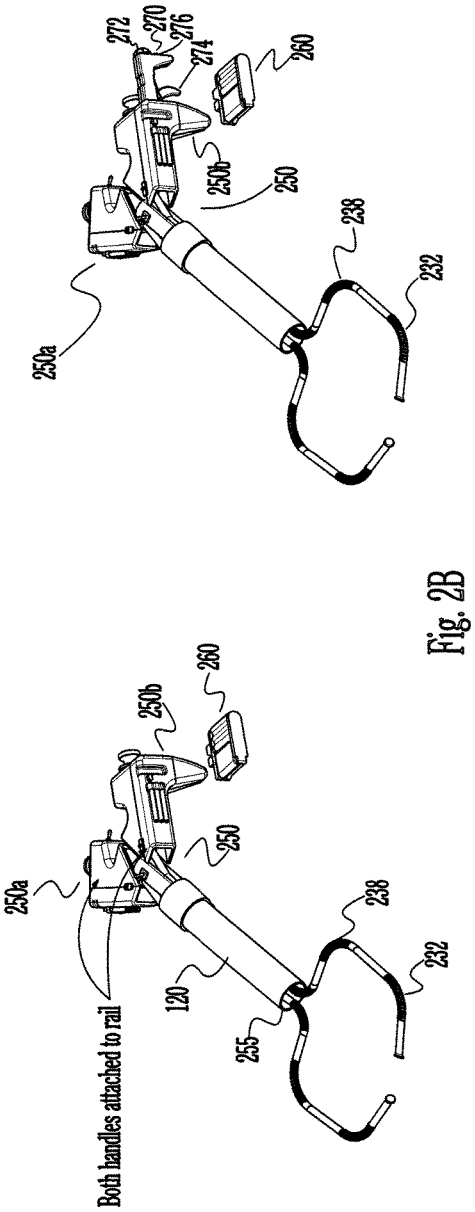
Fig. 2A
Fig. 2B

SYSTEM AND METHOD FOR PERFORMING SURGICAL PROCEDURES WITH A MODULAR SURGICAL SYSTEM HAVING A RAIL MECHANISM

CROSS REFERENCE TO RELATED APPLICATION

This application is a Continuation of U.S. patent application Ser. No. 13/412,055 filed Mar. 5, 2012, which claims benefit of and priority to U.S. Provisional Application No. 61/468,858 filed Mar. 29, 2011, and the disclosures of each of the above-identified applications are hereby incorporated by reference in their entirety.

BACKGROUND

Technical Field

The present disclosure relates generally to the field of reposable or reusable surgical instruments. In particular, the disclosure relates to instruments having separable and replaceable components to provide clean, sterile or refurbished surfaces in each instance of use.

Background of Related Art

Surgical instruments are commonly used in open and endoscopic surgical procedures to coagulate, cauterize and seal tissue. Such surgical instruments may typically include a pair of jaws that can be controlled by a surgeon to grasp targeted tissue, such as, e.g., a blood vessel. The jaws may be approximated to apply a mechanical clamping force to the tissue, and are associated with at least one electrode surface to permit the delivery of electrosurgical energy to the tissue. The combination of the mechanical clamping force and the electrosurgical energy has been demonstrated to join adjacent layers of tissue captured between the jaws. When the adjacent layers of tissue include the walls of a blood vessel, sealing the tissue may result in hemostasis. Thereafter, the sealed tissue may be transected by advancing a knife through the jaws.

In use, various tissue-contacting components of surgical instruments tend to become contaminated or degraded. For example, electrodes may become contaminated as portions of the treated tissue adhere to the tissue-contacting surfaces of the electrodes. Also, a knife blade may become dull and less effective in transecting sealed tissue after repeated use, even in a single surgical procedure. In order to provide clean electrodes and a sharp knife for a particular surgical procedure, a brand new instrument is often used. Once the procedure is complete, the used instrument is discarded.

Surgical instruments that are reposable, or reusable for multiple procedures, reduce the instrumentation costs per procedure. Providing a reusable surgical instrument, however, presents various challenges. For example, the complexity of a surgical instrument tends to result in fairly labor intensive cleaning procedures to prepare the surgical instrument for subsequent use. Improper cleaning may result in dangerous contamination being introduced into the surgical site. Also, some reusable surgical instruments have removable and replaceable components to provide clean surfaces for each use. Many of these surgical instruments require arduous disassembly and reassembly procedures that require extensive training, and may discourage use of the instrument.

SUMMARY

Accordingly, an improved surgical system is provided. The surgical system includes a reusable handle assembly having a controller; a reusable cannula assembly configured to be operatively connected to and steerable by the reusable handle assembly; a rail mechanism configured to cooperate with a port inserted through an incision, the rail mechanism mechanically attached to a stable platform; and a plurality of surgical instruments configured to be inserted through the reusable handle assembly and configured to advance a length of the reusable cannula assembly, such that the plurality of surgical instruments are engaged with at least one trigger mechanism of the reusable handle assembly; wherein the handle assembly, the cannula assembly, and the plurality of surgical instruments are modular components configured to be releasably coupled to each other; and wherein the reusable cannula assembly slidably engages the rail mechanism to extend through the port and into the incision.

In another exemplary embodiment, an improved surgical system is provided. The surgical system includes a modular handle assembly including a joystick controller, a self-contained battery pack, electronic circuitry, and a motor; a modular cannula assembly configured to be releasably secured to and steerable by the modular handle assembly; a rail mechanism configured to cooperate with a port inserted through an incision, the rail mechanism mechanically attached to a stable platform; and a plurality of surgical instruments configured to be inserted through the modular handle assembly and configured to advance a length of the modular cannula assembly, such that the plurality of surgical instruments are releasably secured to the modular handle assembly; wherein releasable securement is caused by a plurality of mechanical mating mechanisms disposed at proximal and/or distal ends of the modular handle assembly, the modular cannula assembly and the plurality of surgical instruments to enable releasable coupling of the assemblies and instruments; and wherein the reusable cannula assembly slidably engages the rail mechanism to extend through the port and into the incision.

In another exemplary embodiment a method of performing a surgical procedure is provided. The method includes the steps of releasably securing a modular handle assembly to a modular cannula assembly, the modular handle assembly including a joystick controller, a self-contained battery pack, electronic circuitry, and a motor; inserting at least one surgical instrument through the modular handle assembly; advancing the at least one surgical instrument a length of the modular cannula assembly; releasably securing the at least one surgical instrument to the modular handle assembly; slidably engaging and releasably securing the cannula assembly to a rail mechanism configured to cooperate with a port inserted through an incision and mechanically attached to a stable platform; and steering the modular cannula assembly via the joystick controller of the modular handle assembly so as to actuate the at least one surgical instrument.

BRIEF DESCRIPTION OF THE DRAWINGS

The accompanying drawings, which are incorporated in and constitute a part of this specification, illustrate embodiments of the disclosure and, together with a general description of the disclosure given above, and the detailed description of the embodiment(s) given below, serve to explain the principles of the disclosure, wherein:

FIGS. 2A and 2B illustrate a method of attaching multiple components of a surgical system with a port and rail mechanism, in accordance with the present disclosure.

DETAILED DESCRIPTION

Figure 1:
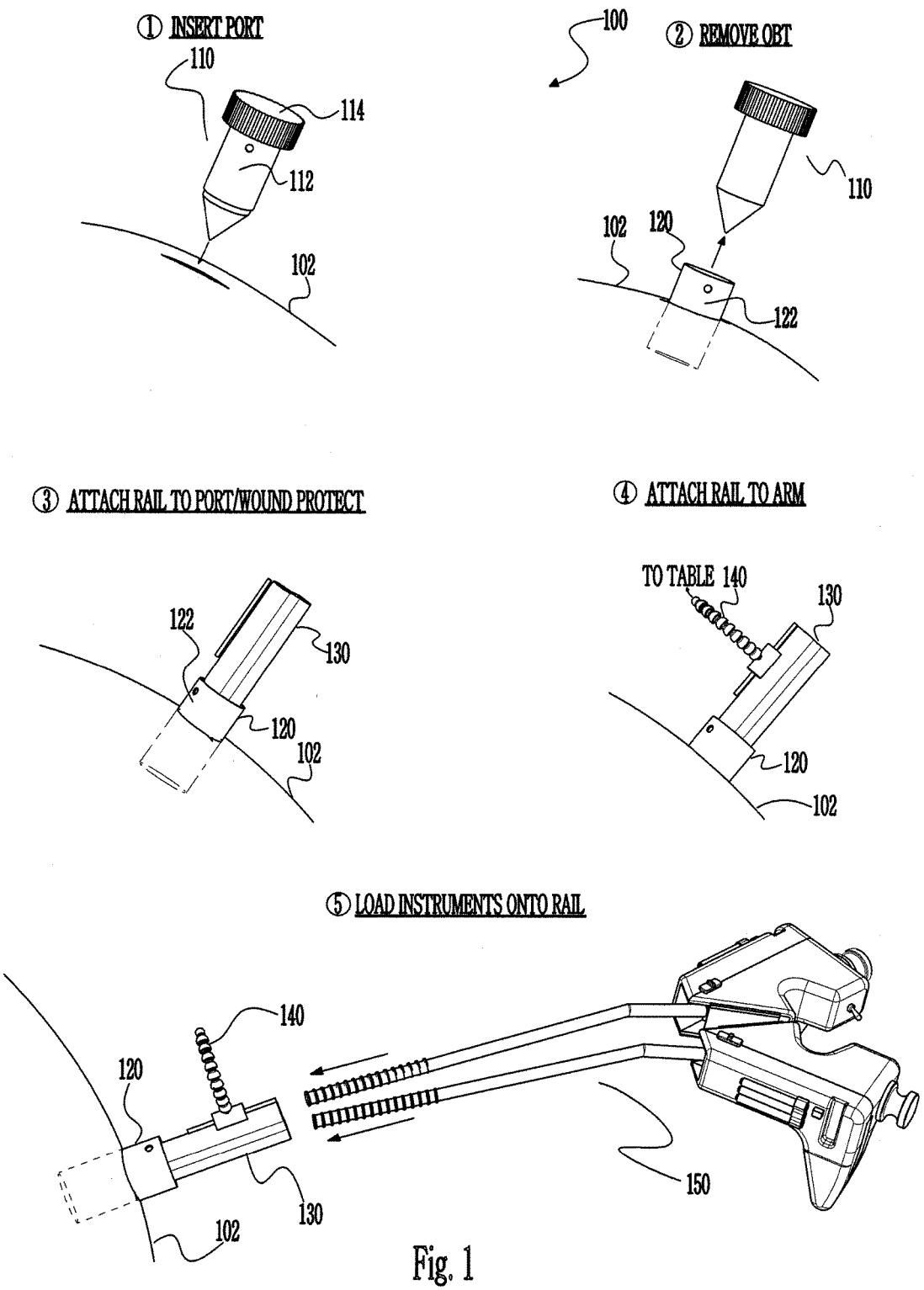
FIG. 1 illustrates a method of attaching a surgical system to a rail mechanism, in accordance with the present disclosure.

Embodiments of the presently disclosed apparatus will now be described in detail with reference to the drawings, in which like reference numerals designate identical or corresponding elements in each of the several views. As used herein, the term "distal" refers to that portion of the tool, or component thereof which is further from the user while the term "proximal" refers to that portion of the tool or component thereof which is closer to the user.

In the exemplary embodiments of the present disclosure, the surgical system includes: 1) a powered reusable handle assembly with a joystick controller and a self-contained battery pack, 2) a reusable and steerable shape locking cannula assembly and 3) at least one flexible surgical instrument with the ability to swap out and be used within the same reusable handle assembly. The components or units or assemblies are modular and snap together for use and snap apart for cleaning. The cannula assembly is designed to be inserted straight through a single incision and is electronically activated to have a preset "offset" bend, which modifies the angle of approach to be lateral within the abdomen of a patient. Flexible surgical instruments are then guided down and follow the inside shape of the cannula assembly. Distal articulating linkages are then steered using the joystick controller to gain precise movement in and around the target surgical site.

In the exemplary embodiments of the present disclosure, through a single incision, the ability to provide lateral traction inside the abdomen without instrument crossover/clashing is achieved. Hand separation and comfort to the end user through powered controls as opposed to manual wrist operation is also achieved. The modular design of the components/assemblies results in cost efficiency by reusing a single motor repeatedly.

Additionally, in the exemplary embodiments of the present disclosure, a rail mechanism or configuration is provided to be inserted through an incision of an abdomen of a patient. The rail mechanism is attached proximally to a floor or table mount in order to create a stable platform. Right and left powered modular handles, with attached steerable cannulas, slide along the rail mechanism, thus allowing movement toward and away from the patient. The right and left powered handle assemblies may be releasably secured to the rail mechanism (coupling configuration). Additionally, the center portion of the rail mechanism may allow for passage of a laparoscopic camera and/or any other type of auxiliary instruments. The rail mechanism provides stability and the opportunity for a surgeon to lock the cannula assembly in place, thus freeing up hands to operate a camera and/or auxiliary instruments.

Referring to FIG. 1, a method of attaching a surgical system to a rail mechanism, in accordance with the present disclosure is illustrated. Surgical method 100 includes a trocar 110 including a body portion 112 and a head portion 114, as shown in step 1. The trocar 110 is used to position a port 120 into an incision 102 of, for example, an abdomen of a patient, as shown in step 2. The port 120 may include an opening 122 for receiving a protrusion of a rail mechanism 130. The rail mechanism 130 slidably engages the port 120 and attaches to the port 120 via the opening 122, as shown in step 3. After the rail mechanism 130 releasably or removably attaches to the port 120, an arm mechanism 140 is attached to the rail mechanism 130, as shown in step 4. Subsequently, as the rail mechanism 130 is stabilized to the port 120 and the arm mechanism 140 is stabilized to the rail mechanism 130, surgical system 150 may be inserted through the rail mechanism 130 and advance through the port 120 and into the incision 102, as shown in step 5.

Figure 3:
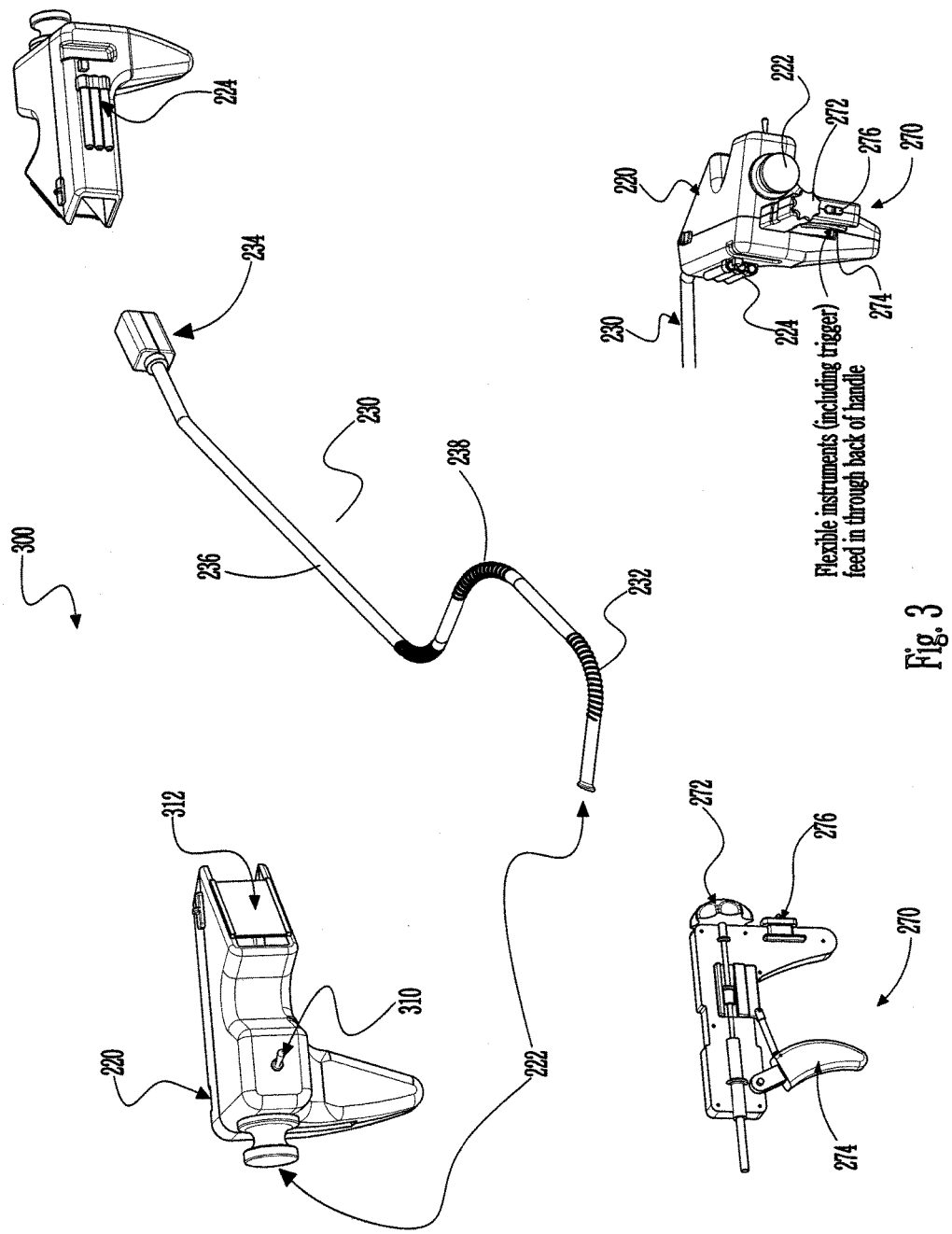
FIG. 3 illustrates several components of a surgical system, including a dovetail interface component on the handle assembly, in accordance with the present disclosure.

The rail mechanism 130 defines a lumen extending therethrough for receiving the reusable cannula assembly 230 (see FIGS. 2A and 2B). Additionally, the rail mechanism 130 may define a plurality of lumens therethrough for receiving a plurality of reusable cannula assemblies 230. The rail mechanism 130 may releasably secure a plurality of reusable cannula assemblies 230 via the dovetail interface 312 (see FIG. 3). In an alternative embodiment, the rail mechanism 130 defines three channels. A first channel for receiving a portion of a first surgical instrument, a second channel for receiving a portion of a second surgical instrument, and a third channel, centrally positioned, for receiving an image capturing unit, such as a camera. The stable platform used to stabilize the rail mechanism 130 via the arm mechanism 140 may be a floor platform or a table platform.

Referring to FIGS. 2A and 2B, a method of attaching multiple components of a surgical system with a port and rail mechanism, in accordance with the present disclosure is presented.

FIG. 2A of method 200 illustrates modular components connected together, whereas FIG. 2B of method 200 illustrates the battery pack and surgical instrument connected to or communicating with the modular components.

Initially, the port 120 is inserted through the incision 102 (see FIG. 1) and is slidably connected or engaged with the rail mechanism 130. The rail mechanism 130 may include a protrusion member 210 for connecting to the arm mechanism 140 (see FIG. 1). Additionally, the rail mechanism 130 may include two channels or passages, one for receiving the surgical instrument 270 and one for receiving either a camera or an auxiliary instrument. Once the rail mechanism 130 snaps into place with the port 120 via the opening 122 (see FIG. 1), the modular components of the surgical system 150 may be assembled. For example, the modular handle assembly 220 may releasably attach to or engage with the modular cannula assembly 230.

The modular handle assembly 220 may include a joystick controller 222 and a motor 224. The modular handle assembly 220 may also include a battery (not shown) and electronic circuitry (not shown) incorporated in the handle portion 226. The modular handle assembly 220 is also configured to include the battery and the motor 224 incorporated therewith for powering the surgical systems 150, 250. The electronic circuitry may electrically communicate with at least one processor for enabling flow of electrosurgical energy between the battery and the motor 224. The joystick controller 222 is configured to steer the plurality of articulation linkages 232 distally disposed on the reusable cannula assembly 230.

The articulation linkages 232 may be flexible segments, which are of equal length relative to each other or which are of different length relative to each other. The plurality of articulation linkages 232, distally disposed, facilitate the bending of a portion of the surgical instrument 270 via the controller 222, described below. Additionally, the modular cannula assembly 230 may include linkages 238 that are not controlled by the controller 222. The linkages 238 may define a pre-set bend. Thus, the articulating linkages 232 are disposed at the distal-most portion of the modular cannula assembly 230 operated/controlled by switch 310 (see FIG. 3).

The modular cannula assembly 230 may include a shaft portion 236 connected between the linkages 238 at a distal end of the shaft 236 and an articulation assembly 234 at a proximal end of the shaft 236.

Once the modular handle assembly 220 is releasably attached or engaged to the modular cannula assembly 230, such connected components may be inserted through or attached to the rail mechanism 130. The distal end of the shaft 236 having the linkages 238 may slidably engage the rail mechanism 130 and advance through the port 120 and into the incision 102 of the patient (see FIG. 1).

FIG. 2B, illustrates two surgical system assemblies 250 interacting with the rail mechanism 130 and the port 120. As depicted, one surgical system 250a slidably engages the left portion of the rail mechanism 130 and another surgical system 250b slidably engages the right portion of the rail mechanism 130. Both surgical systems 250 include a handle assembly 220 and a cannula assembly 230. Additionally, the articulation linkages 232 and the linkages 238 of the modular cannula assembly 230 extend past the distal end 255 of the port 120 in order to access the interior of the incision 102 of the patient. Moreover, a remote battery pack 260, which houses a controller board may be provided to electrically cooperate with the surgical system assembly 250.

A mating mechanism 240 (see FIG. 2A) enables snapping or interconnecting with the articulation assembly 234. The mating mechanism 240 may include a plurality of spaced protrusions and a plurality of spaced recesses for enabling snapping or interconnecting with the reusable handle assembly 220. The articulation assembly 234 may also include a plurality of protrusions and/or recesses for enabling its connection with the mating mechanism 240. It is noted that the connection is a releasable or removable or detachable connection, in order to allow the components to be modular components. Thus, releasable securement is caused by the mechanical mating mechanism 240, which may be incorporated on proximal and/or distal ends of the reusable handle assembly 220, the reusable cannula assembly 230, and/or the surgical instrument 270.

Therefore, the surgical systems 150, 250 include a reusable handle assembly 220 having a joystick controller 222, a reusable cannula assembly 230 configured to be operatively and detachably connected to and steerable by the reusable handle assembly 220, and a rail mechanism 130 configured to cooperate with the port 120 inserted through the incision 102, the rail mechanism 130 mechanically attached to a stable platform via an arm mechanism 140 having a protrusion member 210. Additionally, a plurality of surgical instruments 270 are configured to be inserted through the reusable handle assembly 220 and configured to advance a length of the reusable cannula assembly 230, such that the plurality of surgical instruments 270 are engaged with at least one trigger mechanism 274 of the reusable handle assembly 220.

The handle assembly 220, the cannula assembly 230, the rail mechanism 130, and the plurality of surgical instruments 270 are modular components configured to be releasably or removably or detachably interconnected with each other. Moreover, the reusable cannula assembly 230 is configured to slidably engage the rail mechanism 130 to extend through the port 120 and into the incision 102.

FIG. 2B, further illustrates a surgical instrument 270 inserted through the proximal end of the modular handle assembly 220. The surgical instrument 270 may include an actuation mechanism 272, a trigger mechanism 274, and a ratchet release mechanism 276.

Referring to FIG. 3A, several components of a surgical instrument are presented, including a dovetail interface component on the handle assembly, in accordance with the present disclosure.

The components 300 depict a modular handle assembly 220 including a joystick controller 222. Additionally, the modular handle assembly 220 includes a switch 310, which activates an initial offset bend of the modular cannula assembly 230 and a dovetail interface 312, which is configured to slidably engage the rail mechanism 130 (see FIG. 1).

The components 300 also depict the modular cannula assembly 230 having a shaft 236 connected between the proximal end and the distal end. The proximal end has an articulation assembly 234 and the distal end has a plurality of articulation linkages 232, distally disposed. Additionally, the motor 224 is shown incorporated or embedded within the modular handle assembly 220.

The components 300 also depict a cut-away view of the surgical instrument 270 having the actuation mechanism 272, the trigger mechanism 274, and the ratchet release mechanism 276. The actuation mechanism 272 may be a rotational knob. However, one skilled in the art may contemplate using a plurality of different actuation means for driving the cables in the articulation assembly 234 for moving the plurality of articulation linkages 232, distally disposed.

The components 300 also depict the releasable combination of the components. For example, the surgical instrument 270 is inserted through the back portion of the modular handle assembly 220 and advances through the cannula assembly 230. The joystick controller 222 is also shown positioned on a rear portion of the handle assembly 220. Moreover, it is shown that the surgical instrument 270 advances just enough so that the trigger mechanism 274 and the actuation mechanism 272 protrude from the rear portion of the modular handle assembly 220.

Therefore, one method of the exemplary embodiments includes releasably securing a modular handle assembly 220 to a modular cannula assembly 230, the modular handle assembly 220 including a joystick controller 222, a self-contained battery pack, electronic circuitry, and the motor 224, inserting at least one surgical instrument 270 through the modular handle assembly 220, advancing the at least one surgical instrument 270 a length of the modular cannula assembly 230, releasably securing the at least one surgical instrument 270 to the modular handle assembly 220, slidably engaging and releasably securing the cannula assembly 230 to the rail mechanism 130 configured to cooperate with the port 120 inserted through the incision 102 and mechanically attached to a stable platform and steering the modular cannula assembly 230 via the joystick controller 222 of the modular handle assembly 220 so as to actuate the at least one surgical instrument 270.

In an alternative embodiment, the reusable handle assembly 220 may include at least one sensor positioned thereon or therewith. For example, electrical contacts, proximity sensors, optical sensors, photo diodes, and/or mechanical or metallic sensors may be used to control and/or record information concerning an end effector assembly or the articulation linkages 232 distally disposed or the coupling relationships established between the components of the surgical systems 150, 250.

In yet another alternative embodiment, the reusable handle assembly 220 may include at least one indicator configured to indicate at least one parameter related to the reusable cannula assembly 230 and the plurality of surgical instruments 270.

The at least one indicator may be either a numerical indicator or a color indicator or a combination thereof.

The at least one parameter may relate to positional orientations of a plurality of articulation linkages 232 distally disposed on the reusable cannula assembly 230, may relate to battery pack life, may relate to end-of-life of the reusable handle assembly 220 after a predetermined number of replacements exceed a predetermined limit, may relate to actuations of the surgical instrument 270, and may also relate to coupling relationships established between the reusable handle assembly 220, the reusable cannula assembly 230, and the plurality of surgical instruments 270.

Additionally, the load or loads on battery pack and motor 224 of powered surgical systems 150, 250 are determined to control a motor speed if the load or loads indicate a damaging limitation is reached or approached. For example, the energy remaining in battery pack, the number of firings remaining, whether battery pack must be replaced or charged, and/or approaching the potential loading limits of powered surgical systems 150, 250 may be determined.

While several embodiments of the disclosure have been shown in the drawings, it is not intended that the disclosure be limited thereto, as it is intended that the disclosure be as broad in scope as the art will allow and that the specification be read likewise. Therefore, the above description should not be construed as limiting, but merely as exemplifications of presently disclosed embodiments. Thus the scope of the embodiments should be determined by the appended claims and their legal equivalents, rather than by the examples given.

Persons skilled in the art will understand that the devices and methods specifically described herein and illustrated in the accompanying drawings are non-limiting exemplary embodiments. The features illustrated or described in connection with one exemplary embodiment may be combined with the features of other embodiments. Such modifications and variations are intended to be included within the scope of the present disclosure. As well, one skilled in the art will appreciate further features and advantages of the present disclosure based on the above-described embodiments. Accordingly, the present disclosure is not to be limited by what has been particularly shown and described, except as indicated by the appended claims.

The invention claimed is:

1. A surgical system comprising:
a port configured to be received through an incision, the port defining an opening;
a rail mechanism configured to be secured to the port, the rail mechanism defining at least one lumen extending therethrough, the at least one lumen being coaxial with the opening of the port;
a cannula configured to be received through the port and secured to the rail mechanism;
a handle operatively connected to the cannula, the handle being configured to steer the cannula; and
at least one surgical instrument configured to be inserted through the handle and configured to advance along a length of the cannula, wherein the handle, the cannula, the rail mechanism, and the at least one surgical instrument are modular components configured to be releasably coupled to each other.

2. The surgical system of claim 1, wherein the handle is reusable.

3. The surgical system of claim 1, wherein the handle includes at least trigger mechanism.

4. The surgical system of claim 1, wherein the cannula is reusable.

5. The surgical system of claim 1, wherein the cannula is configured to slidably engage the rail mechanism to extend through the port and into the incision.

6. The surgical system of claim 1, wherein the handle includes a self-contained battery pack and a motor incorporated therewith for powering the surgical system.

7. The surgical system of claim 6, wherein the reusable handle includes electronic circuitry electrically communicating with at least one processor for enabling flow of electrosurgical energy between the battery pack and the motor.

8. The surgical system of claim 1, wherein the handle includes at least one switch for activating an initial offset bend of the reusable cannula.

9. The surgical system of claim 1, wherein handle includes a controller, the controller including a joystick mechanism configured to steer a plurality of articulation linkages distally disposed on the cannula.

10. The surgical system of claim 1, wherein the handle includes a mechanical mating mechanism for enabling coupling with the cannula.

11. The surgical system of claim 1, wherein the cannula includes a plurality of articulation linkages at a distal end thereof.

12. The surgical system of claim 11, wherein the plurality of articulation linkages are flexible segments.

13. The surgical system of claim 12, wherein the plurality of articulation linkages facilitate bending of a portion of the at least one surgical instrument.

14. The surgical system of claim 13, wherein the cannula includes an articulation assembly at a proximal end thereof for interfacing with at least one cable for steering the plurality of articulation linkages distally disposed.

15. The surgical system of claim 1, wherein the at least one surgical instrument includes a proximal end, a flexible shaft connected to the proximal end, and an end effector connected at a distal end of the flexible shaft.

16. The surgical system of claim 11, wherein the at least one surgical instrument includes at least one mechanical mating mechanism for mating with the handle.

17. The surgical system of claim 16, wherein the at least one mechanical mating mechanism includes a plurality of spaced protrusions and a plurality of spaced recesses for enabling coupling with the handle.

18. The surgical system of claim 11, wherein the end effector assembly includes a pair of opposed jaw members such that at least one of the jaw members is induced to move relative to the other jaw member between open and closed positions in response to manipulation of the reusable handle.

19. The surgical system of claim 1, wherein the handle includes at least one sensor positioned thereabout.

20. The surgical system of claim 1, wherein the handle includes at least one indicator configured to indicate at least one parameter related to the cannula and the at least one surgical instrument.

* * * * *